(12) United States Patent
Hamrock

(10) Patent No.: US 6,863,838 B2
(45) Date of Patent: Mar. 8, 2005

(54) ZWITTERIONIC IMIDES

(75) Inventor: Steven Joseph Hamrock, Stillwater, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 144 days.

(21) Appl. No.: 10/041,998

(22) Filed: Oct. 25, 2001

(65) Prior Publication Data

US 2003/0087151 A1 May 8, 2003

(51) Int. Cl.[7] .......................... H01G 35/00; H01M 6/04; C07C 303/00; C07D 277/04; C07D 211/02
(52) U.S. Cl. ........................ 252/62.2; 429/200; 564/82; 548/146; 546/249
(58) Field of Search ........................ 252/62.2; 429/200; 564/82; 548/146; 546/249

(56) References Cited

U.S. PATENT DOCUMENTS

| | | | |
|---|---|---|---|
| 4,505,997 A | | 3/1985 | Armand et al. |
| 5,072,040 A | | 12/1991 | Armand |
| 5,273,840 A | | 12/1993 | Dominey |
| 5,463,005 A | | 10/1995 | Desmarteau |
| 5,514,493 A | | 5/1996 | Waddell et al. |
| 5,652,072 A | | 7/1997 | Lamanna et al. |
| 5,723,664 A | * | 3/1998 | Sakaguchi et al. ............ 564/82 |
| 5,827,602 A | | 10/1998 | Koch et al. |
| 5,879,828 A | | 3/1999 | Debe et al. |
| 5,965,054 A | | 10/1999 | McEwen et al. |
| 6,063,522 A | | 5/2000 | Hamrock et al. |
| 6,090,895 A | | 7/2000 | Mao et al. |

FOREIGN PATENT DOCUMENTS

WO    WO 99 49529 A    9/1999

OTHER PUBLICATIONS

U. Jäger, W. Sundermeyer, H. Pritzkow; "Zur Synthese Perfluorierter Sulfimide, $R_fN=SO_2$, und Deren Stabilisierung Durch Tertiäre Amine", Chem. Ber., vol. 120, (1987), pp. 1191–1195.

R. Albrecht and Gänter Kresze; "Umsetzung Mit Pyridin–N–Oxiden und Diphenylnitron", Chem. Ber., vol. 98, No. 4, (1965), pp. 1205–1209.

F. Boberg, G. Nink, B. Bruchmann, and A. Garming; "Reaktionen Von Thioxoheterocyclen Mit N–Chloramiden IV. N–Phenylsulfonyl–S–Pyridiniosulfoximidate Und N–(Phenylsulfonyl)Pyridinium–Sulfonamidate", Phosphorus, Sulfur, and Silicon; vol. 57, (1991), pp. 235–247.

F. Boberg, B. Bruchmann, A. Herzberg, and A. Otten; "Reaktionen Von Thioxoverbindungen Mit N–Chloramiden VI. Thiochinolone, Dihydrothiazolthione Und Dihydroisothiazolthione Mit Natrium–N–Chlorbenzolsulfonamiden", Phosphorous, Sulfur, and Silicon; vol. 108, (1996), pp. 203–220.

F. Boberg, and A. Otten; "Reaktionen Von Thioxoverbindungen Mit N–Chloramiden VII. 5,5–Dimethyl–3–Dimethylamino–2–Cyclohexen–1–Thion Und 3–Dimethylamino–1–Phenyl–2–Prpen–1–Thion Mit Natrium–N–Chlorbenzolsulfonamiden", Phosphorous, Sulfur, and Silicon; vol. 112, (1996), pp. 91–99.

Von R. Appel, and R. Helwerth; "Derivate des Imidobissulfamids", Angewandte Chemie, vol. 79, No. 21, (1967), pp. 937–938.

Patent Abstracts of Japan; vol. 2000, No. 25, Apr. 12, 2001.

Argyropoulos, D., and Lenk, R. S., *Condensation Products from Imidobis(sulfury lChloride)*, Journal of Applied Polymer Science, vol. 26, (1981), pp. 3073–3–84.

Roesky, Von H. W., and Giere, H. H., *Darstellung von N–Trifluormethansulfonyl–sulfonylfluoridamid und einige reaktionen 1*, Inorg. Nucl. Chem. Letters, vol. 7, pp. 171–175, (1971) Pergannon Press.

*Imidodisulfuric Acid Chloride*, Inorganic Syntheses, vol. VIII, (1955), pp. 105–107.

Doyle, M., Choi, S. K., and Proulx, G., *High–Temperature Proton Conducting Membranes Based on Perfluorinated Ionomer Membrane–Ionic Liquid Composites*, Journal of the Electrochemical Society, 147, (1), (2000), pp. 34–37.

* cited by examiner

Primary Examiner—Deborah C. Lambkin
(74) Attorney, Agent, or Firm—Philip Y. Dahl

(57) ABSTRACT

Zwitterionic imide compounds are provided according to the formula: $R_1$—$SO_2$—$N^-$—$SO_2$—$R_2^+$, where $R_1$ and $R_2^+$ are any suitable groups. Typically $R_1$ is a highly fluorinated alkane and $R_2^+$ contains a quaternary ammonium group or a heteroatomic aromatic group having an cationic nitrogen, such as: pyridiniumyl, pyridaziniumyl, pyrimidiniumyl, pyraziniumyl, imidazoliumyl, pyrazoliumyl, thiazoliumyl, oxazoliumyl, or triazoliumyl. Zwitterionic liquids are provided, typically having melting points of less than 100° C. and typically having a solubility in water of less than 5% by weight.

30 Claims, No Drawings

ZWITTERIONIC IMIDES

FIELD OF THE INVENTION

This invention relates to zwitterionic imide compounds according to the formula: $R_1$—$SO_2$—$N^-$—$SO_2$—$R_2^+$ and zwitterionic liquids having a melting point of less than 100° C.

BACKGROUND OF THE INVENTION

U.S. Pat. No. 5,827,602 and U.S. Pat. No. 5,965,054 disclose non-aqueous ionic liquids for use as electrolytes that are based on salts composed of separate anion and cation moieties. The cation moieties are selected from pyridinium, pyridazinium, pyrimidinium pyrazinium, imidazolium, pyrazolium, thiazolium, oxazolium, and triazolium ions.

U.S. Pat. No. 6,090,895 discloses crosslinked polymers having imide crosslinking groups and methods of crosslinking polymers to form imide crosslinking groups. These crosslinked polymers may be useful as polymer electrolyte membranes (PEM's) in fuel cells.

U.S. Pat. Nos. 6,063,522, 4,505,997, 5,652,072, 5,072,040 and 5,514,493 disclose electrolytes comprising imide functional groups.

U.S. Pat. No. 5,463,005 discloses perfluorinated monomers and polymers comprising sulfonyl and carbonyl imide groups for use as solid polymer electrolytes.

M. Doyle, S. K. Choi and G. Proulx, J. Electrochem. Soc., 147, 34–37, discloses the use of ethyl methyl imidazolium (EMI) triflate, a low melting ionic liquid composed of separate anion and cation moieties, together with a known sulfonated fluoropolymer (Nafion) to give a fuel cell membrane material for use at elevated temperatures.

SUMMARY OF THE INVENTION

Briefly, the present invention provides a zwitterionic imide compound according to the formula: $R_1$—$SO_2$—$N^-$—$SO_2$—$R_2^+$, where $R_1$ and $R_2^+$ are any suitable groups. Typically $R_1$ is a highly fluorinated alkane and $R_2^+$ is a heteroatomic aromatic group having an cationic nitrogen, such as: pyridiniumyl, pyridaziniumyl, pyrimidiniumyl, pyraziniumyl, imidazoliumyl, pyrazoliumyl, thiazoliumyl, oxazoliumyl, or triazoliumyl. Typically the zwitterionic imide has a melting point of less than 100° C. Typically the zwitterionic imide compound has a solubility in water of less than 5% by weight.

In another aspect, the present invention provides a zwitterionic liquid having a melting point of less than 100° C. and typically having a solubility in water of less than 5% by weight.

In another aspect, the present invention provides an electrochemical device comprising the zwitterionic liquid or the zwitterionic imide according to the present invention, such as a battery or a fuel cell.

What has not been described in the art, and is provided by the present invention, is an ionic liquid having a melting point of less than 100° C. that is a zwitterionic compound, particularly a zwitterionic imide compound.

In this application:

"highly halogenated", means containing halogen in an amount of 40 wt % or more, but typically 50 wt % or more, and more typically 60 wt % or more; and "highly fluorinated", means containing fluorine in an amount of 40 wt % or more, but typically 50 wt % or more, and more typically 60 wt % or more; and "substituted" means, for a chemical species, substituted by conventional substituents which do not interfere with the desired product or process, e.g., substituents can be alkyl, alkoxy, aryl, phenyl, halo (F, Cl, Br, I), cyano, nitro, etc.

It is an advantage of the present invention to provide an electrolyte for use in electrochemical devices such as batteries and fuel cells at temperatures in excess of 80° C. The zwitterionic liquids can be more stable in use than conventional (non-zwitterionic) ionic liquids, since they do not form a neutral, volatile, water soluble species upon protonation of the anion.

DETAILED DESCRIPTION OF PREFERRED EMBODIMENTS

The present invention provides zwitterionic imide compounds according to the formula: $R_1$—$SO_2$—$N^-$—$SO_2$—$R_2^+$, where $R_1$ and $R_2^+$ are any suitable groups. Typically $R_1$ is a highly fluorinated alkane and $R_2^+$ contains a heteroatomic aromatic group having an cationic nitrogen, such as: pyridiniumyl, pyridaziniumyl, pyrimidiniumyl, pyraziniumyl, imidazoliumyl, pyrazoliumyl, thiazoliumyl, oxazoliumyl, or triazoliumyl.

The present invention additionally provides a zwitterionic liquid having a melting point of less than 100° C. and typically having a solubility in water of less than 5% by weight, which may be a zwitterionic imide compound according to the present invention.

Electrochemical devices such as batteries and fuel cells employ electrolyte materials to conduct ions participating in electrochemical reactions. Common aqueous based electrolytes are not suitable for use at high temperatures in excess of 100° C., since the water component can evaporate. Drying of the electrolyte can become a problem at temperatures of 80° C. or greater.

Polymer electrolyte membranes (PEM's) may be used in electrochemical devices, particularly in fuel cells. PEM's are composed of a polymer backbone, typically fluorinated, having pendant acidic groups such as sulfonic acid groups. Examples include Nafion® (DuPont Chemicals, Wilmington Del.) and Flemion™ (Asahi Glass Co. Ltd., Tokyo, Japan). Non-fluorinated PEMS's include sulfonated polysulfone and sulfonated PEEK. In a fuel cell, the PEM conducts H+ ions (protons) while forming a barrier to the passage of reactant gasses ($H_2$ and $O_2$). The PEM is electrically non-conductive. However, membranes of these polymers must contain a liquid electrolyte, typically water, to function electrolytically. Even though water is produced during the electrochemical reactions carried out in a hydrogen fuel cell, drying of the PEM can become a problem at temperatures of 80° C. or greater and the cell cannot operate with a water electrolyte at temperatures in excess of 100° C.

Conventional (non-zwitterionic) ionic liquids can be of limited utility in extreme environments where the anion can become protonated. The resulting neutral acid may be volatile and water soluble. This is a particular concern for fuel cell use, since a volatile, water soluble species will be washed out of the cell, rendering it inactive.

The zwitterionic liquids according to the present invention can be used as electrolytes in electrochemical devices such as batteries and fuel cells. The zwitterionic liquids may be used neat or with a solvent, diluent or additive. Additives may be used to alter melting point, viscosity, ionic conductivity, and the like. Further, the zwitterionic liquids according to the present invention can be absorbed into polymer electrolyte membranes for use in electrochemical devices, especially for use in fuel cells. The zwitterionic liquids may be substituted for water in a typical polymer electrolyte membrane by any suitable method. In one method, the zwitterionic liquid is applied to the membrane and/or the membrane is immersed in the zwitterionic liquid, with these steps being repeated as necessary.

The zwitterionic liquids according to the present invention typically have a melting point of less than 100° C., more typically less than 80° C., more typically less than 60° C., and most typically less than 40° C. The zwitterionic liquids according to the present invention typically have a solubility in water of less than 5% by weight, more typically less than 1% by weight, and most typically less than 0.1% by weight.

In one embodiment, the zwitterionic liquid according to the present invention is a zwitterionic imide compound according to formula (I):

$$R_1-SO_2-N^--SO_2-R_2^+ \qquad (I)$$

where $R_1$ and $R_2^+$ are any suitable groups.

$R_1$ may be any group which does not interfere with the desired characteristics of the compound. $R_1$ may be selected from straight-chain, branched, cyclic and aromatic groups, including saturated and unsaturated groups, including heteroatomic groups, and including any of the above which are substituted. Typically $R_1$ is a highly halogenated alkane, more typically a highly fluorinated alkane. More typically $R_1$ is a perhalogenated alkane, and most typically a perfluorinated alkane. Typically $R_1$ contains between 1 and 20 carbon atoms, more typically between 1 and 8 carbon atoms, and most typically between 1 and 4 carbon atoms.

$R_2^+$ may be any cationic group which does not interfere with the desired characteristics of the compound. $R_2^+$ may be selected from straight-chain, branched, cyclic and aromatic groups, including saturated and unsaturated groups, including heteroatomic groups, and including any of the above which are substituted. Typically, $R_2^+$ is an aromatic group, more typically an aromatic heterocyclic group. More typically, $R_2^+$ is a cationic heteroatomic aromatic group including nitrogen. More typically, $R_2^+$ is selected from the following:

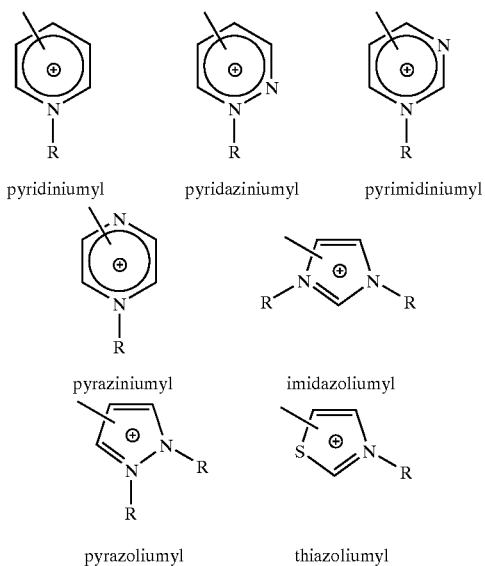

pyridiniumyl   pyridaziniumyl   pyrimidiniumyl pyraziniumyl   imidazoliumyl pyrazoliumyl   thiazoliumyl -continued

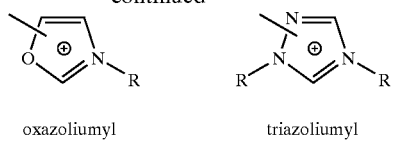

oxazoliumyl   triazoliumyl where R groups are independently selected from H, alkyl, haloalkyl, fluoroalkyl, or any group which does not interfere with the desired characteristics of the compound. R may be selected from straight-chain, branched, cyclic and aromatic groups, including saturated and unsaturated groups, including heteroatomic groups, and including any of the preceding which are substituted. Typically R contains between 0 and 20 carbon atoms, more typically between 0 and 8 carbon atoms, and most typically between 0 and 4 carbon atoms. The above-listed $R_2^+$ groups may be additionally substituted at any available carbon. Substituents may join with each other or with R groups to form additional aromatic or non-aromatic rings. Alternately, the open valence of the $R_2^+$ group, i.e., the imide attachment point, may be on the R group or other substituent, rather than on the aromatic ring as depicted above. Typically, the zwitterionic imide contains an imide bound directly to an aromatic group. The imide may be bound to a carbon or to a nitrogen of the aromatic group.

Alternately, $R_2^+$ may be a quaternary ammonium group. Examples of such quaternary ammonium groups include tetraalkyl ammonium cations. Where $R_2^+$ is a tetraalkyl ammonium group, alkyl substituents of the tetraalkyl ammonium group typically contain 1 to 12 carbons, more typically 1 to 8 carbons, and more typically 1 to 4 carbons. Alkyl substituents of the tetraalkyl ammonium group may be substituted or may link to form ring structures containing the ammonium nitrogen. Alkyl substituents of the tetraalkyl ammonium group may be substituted with polymerizable functional groups. The imide may be bound to a carbon or to the nitrogen of the ammonium group.

The zwitterionic imide according to the present invention can be made by any suitable method. Known imide syntheses may be performed using the appropriate starting materials containing the desired $R_1$ and $R_2^+$ groups, including syntheses described in: U.S. Pat. Nos. 6,063,522, 4,505,997, 5,652,072, 5,072,040, 5,514,493 and 5,463,005, the contents of which are incorporated by reference herein. Useful synthetic routes may include:

$$R_1-SO_2-NH_2+Cl-SO_2-R_2^+ \rightarrow R_1-SO_2-N^--SO_2-R_2^+ \quad (I)$$

$$R_1-SO_2-Cl+H_2N-SO_2-R_2^+ \rightarrow R_1-SO_2-N^--SO_2-R_2^+ \quad (II)$$

It will be recognized that reactions (I) and (II) are typically carried out in the presence of additional base such as $(Et)_3N$.

If desired, the cationic group of $R_2^+$ may be converted with a protecting group during synthesis and unprotected after synthesis.

This invention is useful as an electrolyte in devices such as batteries and fuel cells, particularly high-temperature devices for operation at temperatures in excess of 100° C.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

I claim:

1. A zwitterionic imide compound according to formula (I):

$$R_1\text{—}SO_2\text{—}N^-\text{—}SO_2\text{—}R_2^+ \quad (I)$$

wherein $R_1$ is selected from the group consisting of straight-chain, branched, cyclic and aromatic groups, including saturated and unsaturated groups, including heteroatomic groups, and including any of the above which are substituted; and wherein $R_2^+$ is any cationic group selected from the group consisting of straight-chain, branched, cyclic and aromatic groups, including saturated and unsaturated groups, including heteroatomic groups, and including any of the above which are substituted.

2. The zwitterionic imide compound according to claim 1, wherein $R_2^+$ is an aromatic group.

3. The zwitterionic imide compound according to claim 2, wherein $R_2^+$ is a heterocyclic group.

4. The zwitterionic imide compound according to claim 3, wherein $R_2^+$ contains a cationic nitrogen atom.

5. The zwitterionic imide compound according to claim 1, wherein $R_2^+$ contains a functional group selected from the group consisting of: pyridiniumyl, pyridaziniumyl, pyrimidiniumyl, pyraziniumyl, imidazoliumyl, pyrazoliumyl, thiazoliumyl, oxazoliumyl, and triazoliumyl.

6. The zwitterionic imide compound according to claim 1, wherein $R_2^+$ contains a quaternary ammonium cation.

7. The zwitterionic imide compound according to claim 1, wherein $R_2^+$ contains a tetraalkyl ammonium functional group.

8. The zwitterionic imide compound according to claim 7, wherein alkyl substituents of said tetraalkyl ammonium functional group contain 1 to 8 carbons.

9. The zwitterionic imide compound according to claim 1, wherein $R_1$ is a highly halogenated hydrocarbon group.

10. The zwitterionic imide compound according to claim 1, wherein $R_1$ is a highly fluorinated hydrocarbon group.

11. The zwitterionic imide compound according to claim 8, wherein $R_1$ is a highly halogenated hydrocarbon group.

12. The zwitterionic imide compound according to claim 8, wherein $R_1$ is a highly fluorinated hydrocarbon group.

13. The zwitterionic imide compound according to claim 1 having a melting point of less than 100° C.

14. The zwitterionic imide compound according to claim 10 having a melting point of less than 100° C.

15. The zwitterionic imide compound according to claim 12 having a melting point of less than 100° C.

16. The zwitterionic imide compound according to claim 1 having a solubility in water of less than 5% by weight.

17. The zwitterionic imide compound according to claim 12 having a solubility in water of less than 5% by weight.

18. The zwitterionic imide compound according to claim 15 having a solubility in water of less than 5% by weight.

19. A zwitterionic liquid having a melting point of less than 100° C.

20. The zwitterionic liquid according to claim 19 which is an aromatic zwitterionic liquid.

21. The zwitterionic liquid according to claim 19 having a solubility in water of less than 5% by weight.

22. The zwitterionic liquid according to claim 21 which is an aromatic zwitterionic liquid.

23. A polymer electrolyte membrane having absorbed therein the zwitterionic imide compound according to claim 1.

24. A polymer electrolyte membrane having absorbed therein the zwitterionic imide compound according to claim 8.

25. A polymer electrolyte membrane having absorbed therein the zwitterionic imide compound according to claim 12.

26. A polymer electrolyte membrane having absorbed therein the zwitterionic liquid according to claim 19.

27. An electrochemical device comprising the polymer electrolyte membrane according to claim 23.

28. An electrochemical device comprising the polymer electrolyte membrane according to claim 24.

29. An electrochemical device comprising the polymer electrolyte membrane according to claim 25.

30. An electrochemical device comprising the polymer electrolyte membrane according to claim 26.

* * * * *

UNITED STATES PATENT AND TRADEMARK OFFICE
CERTIFICATE OF CORRECTION

PATENT NO. : 6,863,838 B2
DATED : March 8, 2005
INVENTOR(S) : Hamrock, Steven J.

It is certified that error appears in the above-identified patent and that said Letters Patent is hereby corrected as shown below:

Title page,
Item [56], References Cited, OTHER PUBLICATIONS,
"U. Jäger, W. Sundermeyer, H. Pritzkow;" reference, delete "R$f$N=SO$_2$" and insert
-- R$_f$N=SO$_2$ -- therefore;
"Roesky, Von H. W.," reference, delete "*reaktionen 1*" and insert -- *reaktionen [1]* --
therefore.
Item [57], ABSTRACT,
Line 5, delete "having an cationic" and insert -- having a cationic -- therefore.

Column 2,
Line 19, delete "having an cationic" and insert -- having a cationic -- therefore.
Line 42, delete "PEMS's" and insert -- PEM's -- therefore.

Signed and Sealed this

Twenty-third Day of August, 2005

JON W. DUDAS
*Director of the United States Patent and Trademark Office*